(12) United States Patent
Tankovich

(10) Patent No.: US 7,780,656 B2
(45) Date of Patent: Aug. 24, 2010

(54) PATTERNED THERMAL TREATMENT USING PATTERNED CRYOGEN SPRAY AND IRRADIATION BY LIGHT

(75) Inventor: Nikolai I Tankovich, San Diego, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 990 days.

(21) Appl. No.: 11/297,928

(22) Filed: Dec. 8, 2005

(65) Prior Publication Data

US 2007/0118098 A1 May 24, 2007

Related U.S. Application Data

(60) Provisional application No. 60/635,143, filed on Dec. 10, 2004.

(51) Int. Cl.
*A61B 18/02* (2006.01)
*A61B 18/20* (2006.01)

(52) U.S. Cl. ............................................. 606/20; 606/9

(58) Field of Classification Search .................... 606/9, 606/20, 22–24, 26; 607/88, 89
See application file for complete search history.

(56) References Cited

U.S. PATENT DOCUMENTS

| 4,376,376 A | 3/1983 | Gregory |
| 5,057,104 A | 10/1991 | Chess |
| 5,282,797 A | 2/1994 | Chess |
| 5,336,217 A | 8/1994 | Buys et al. |
| 5,344,418 A | 9/1994 | Ghaffari |
| 5,820,626 A | 10/1998 | Baumgardner |
| 6,050,990 A | 4/2000 | Tankovich et al. |
| 6,059,820 A | 5/2000 | Baronov |
| 6,096,029 A | 8/2000 | O'Donnell, Jr. |
| 6,171,301 B1 | 1/2001 | Nelson et al. |
| 6,248,103 B1 | 6/2001 | Tannenbaum et al. |
| 6,306,119 B1 * | 10/2001 | Weber et al. ................. 604/290 |
| 6,387,089 B1 | 5/2002 | Kreindel et al. |
| 6,413,253 B1 | 7/2002 | Koop et al. |
| 6,475,211 B2 * | 11/2002 | Chess et al. .................... 606/9 |
| 6,514,244 B2 | 2/2003 | Pope et al. |

(Continued)

FOREIGN PATENT DOCUMENTS

WO  WO99/27863  *  6/1999

(Continued)

OTHER PUBLICATIONS

U.S. Appl. No. 60/458,770, filed Mar. 2003, Manstein et al.

(Continued)

*Primary Examiner*—Michael Peffley
*Assistant Examiner*—Samantha Good
(74) *Attorney, Agent, or Firm*—Wood, Herron & Evans, LLP

(57) ABSTRACT

A spray of cryogen is patterned to create a pattern of cooled regions on a target tissue for cosmetic dermatological treatment. In one embodiment, the cryogen is patterned using a heated mask. An optical source is configured to irradiate the target tissue in a region at least partially overlapping the cooled regions to create a pattern of treatment zones. A control unit adjusts the timing of between the cryogen and optical pulses.

19 Claims, 10 Drawing Sheets

U.S. PATENT DOCUMENTS

| | | | |
|---|---|---|---|
| 6,517,532 B1 | 2/2003 | Altshuler et al. | |
| 6,632,219 B1 * | 10/2003 | Baranov et al. | 606/9 |
| 6,706,032 B2 | 3/2004 | Weaver et al. | |
| 6,997,923 B2 | 2/2006 | Anderson et al. | |
| 7,204,832 B2 | 4/2007 | Altshuler et al. | |
| 2001/0009997 A1 * | 7/2001 | Pope et al. | 606/9 |
| 2002/0091377 A1 * | 7/2002 | Anderson et al. | 606/9 |
| 2002/0161357 A1 | 10/2002 | Anderson et al. | |
| 2002/0173780 A1 | 11/2002 | Altshuler et al. | |
| 2003/0036680 A1 | 2/2003 | Black | |
| 2003/0216719 A1 | 11/2003 | Debenedictis et al. | |
| 2004/0002704 A1 | 1/2004 | Knowlton et al. | |
| 2004/0073079 A1 | 4/2004 | Altshuler et al. | |
| 2004/0082941 A1 * | 4/2004 | Connors et al. | 606/9 |
| 2004/0093042 A1 | 5/2004 | Altshuler et al. | |
| 2005/0049582 A1 | 3/2005 | DeBenedictis et al. | |

FOREIGN PATENT DOCUMENTS

| | | |
|---|---|---|
| WO | WO 2004/037068 A3 | 5/2004 |
| WO | WO 2004/086947 A2 | 10/2004 |

OTHER PUBLICATIONS

Fuji, H. et al., "Multispot Laser Photocoagulation System Using a Fiber Bundle Scanner," Applied Optics, Oct. 1, 1982, vol. 21, No. 19.

Manstein, D. et al., "Fractional Photothermolysis: A New Concept for Cutaneous Remodeling Using Microscopic Patterns of Thermal Injury," Lasers in Surgery and Medicine, 2004, pp. 426-438, vol. 34.

International Search Report and Written Opinion, PCT/US05/44878, Aug. 10, 2006, 7 pages.

Anderson et al, U.S. Appl. No. 60/258,855, filed Dec. 28, 2000, pp. 1-3, 5, 6, 8-15 and Figures 22A and 22B.

* cited by examiner

PATTERNED THERMAL TREATMENT USING PATTERNED CRYOGEN SPRAY AND IRRADIATION BY LIGHT

CROSS-REFERENCE TO RELATED APPLICATION

This application claims priority under 35 U.S.C. §119(e) to U.S. Provisional Patent Application Ser. No. 60/635,143, "Spray Fractals Device and Method," by Nikolai I. Tankovich, filed Dec. 10, 2004. The subject matter of the foregoing is incorporated herein by reference in its entirety.

BACKGROUND OF THE INVENTION

1. Field of the Invention

This invention relates generally to creating fractional treatment using a patterned cooling spray and an optical source, for example by using a patterned cryogen spray with a laser source to create a pattern of microscopic treatment zones for cosmetic dermatological treatment.

2. Description of the Related Art

Light sources (e.g., lasers, LEDs, flashlamps, etc., including in the non-visible wavelengths such as infrared) are frequently used to treat biological tissues inside and outside the human body through a photothermal process that comprises heating the tissue using light absorbed by the tissue. In this photothermal process, a target tissue or its constituents absorb the treatment light and convert the light energy into thermal energy to cause thermal damage or stimulation to the tissue.

If photothermal treatment uses a wide beam of light, particularly with a wavelength that is non-selective, such as a wavelength primarily absorbed within the tissue by water, it can be difficult to optimize the parameters to achieve treatment that is both effective and has a low risk of side effects. If the delivered optical fluence is too high, the region can be overtreated, resulting in slow healing and other side effects. If the delivered optical fluence is too low, the stimulation may be too weak to cause the desired treatment. Thus, broad area photothermal treatment is limited in the levels of treatment that are simultaneously effective and safe.

Fractional photothermolysis addresses this limitation of broad area photothermolysis by using a patterned distribution of light to irradiate only a fraction of the tissue with high intensity light. Thus, in fractional photothermolysis, only a portion of the overall target tissue is directly treated, which allows a higher level of treatment in those small areas than would be desired with a broad area treatment. The level of treatment can be adjusted by adjusting the treatment density of treatment within the irradiated area. Treating fractionally allows the light energy to be increased to the point where tissue treatment occurs routinely without causing slow healing and other side effects. Fractional photothermolysis thus accomplishes more reproducible treatment in the treated areas by sparing healthy tissue in the regions between treatment zones.

To improve the uniformity of treatment and to reduce the visibility of the treatment zones when used to treat skin for cosmetic procedures, the treatment zones for fractional phototherapy are typically limited to 50-300 µm in diameter and final treatment densities of 500-3000 treatment zones per $cm^2$ are typically used. To treat large areas at these high densities at commercially viable speeds, a fast scanning system or an array of microlenses may be used. Both of these systems are expensive and can be subject to precise alignment tolerances. In addition, these systems can be painful. In addition, moving parts in the scanning system can wear out, thus reducing reliability.

One limitation of fractional resurfacing technology is that the dermal-epidermal junction (DE junction) is the weakest portion of the skin. High density fractional treatments can lead to separation of the DE junction, which can slow the healing process. Very high density fractional treatments can approach broad area treatment and can suffer from similar side effects. However, using higher density of dermal treatment while limiting treatment coverage at the DE junction is desired for some cosmetic treatments, such as the treatment of wrinkles.

Therefore, there is a need for phototherapy approaches that spare healthy tissue surrounding treatment zones to permit rapid healing with low side effects, avoid the use of complex optical systems and moving parts, reduce the pain associated with fractional laser treatments, and/or reduce limitations on dermal treatment density.

SUMMARY OF THE INVENTION

The shortcomings of the prior art are overcome by delivering a patterned cryogen to target tissue and irradiating the target tissue with light, to create a pattern of treatment zones within the target tissue, for example for purposes of cosmetic dermatological treatment. The approach of patterned cryogen cooling can be used to create patterns of epidermal and dermal sparing.

In one embodiment, the cryogen delivery system includes one or more cryogen containers, and cryogen is delivered to the target tissue either directly or through one or more cryogen delivery tubes. In the optical delivery system, an optical source irradiates the target tissue in a region at least partially overlapping the area where the cryogen is delivered. A control unit controls the timing of the delivery of the patterned cryogen to the target tissue relative to the irradiation of the target tissue by the light. For example, the control unit may control the timing of a cryogen spray relative to pulsing of an optical source. Different timings can be used. For example, the timing can be adjusted such that the cryogen evaporates before the target tissue is irradiated. Alternately, the target tissue can be irradiated after the cryogen has been delivered but before it evaporates. In some embodiments, a mask is used to pattern the cryogen. A cryogen spray is directed at the mask, which selectively blocks parts of the cryogen spray, resulting in a patterned cryogen. The mask may be heated, for example by a circulating fluid or by a resistive heater.

The optical source can be pulsed or continuous wave (CW). The optical source can be, for example, a laser or a flashlamp. The optical source can be a laser emitting light in the wavelength range of 1.4-1.6 µm. The wavelength of the optical source can be selective or non-selective. A second optical source can also irradiate the target tissue and thus provide a second treatment wavelength that is different from the wavelength of the first optical source. In some embodiments, the optical source delivers light through a light guide or through free space. An optional delivery lens may be used to distribute the light as desired.

In some embodiments, the treatment zones are discrete and the density of the treatment zones is 100-4000 per $cm^2$. Alternately, the treatment zones may be overlapping or form a continuous pattern. The treatment zones may comprise regions of coagulated dermal tissue. The patterned cryogen and irradiation can also be designed so that the treatment zones are wider within the dermis than at the DE junction.

Some designs are based on a handpiece. The patterned cryogen and the irradiating light are both delivered through the handpiece. The handpiece may include a velocity- or position-sensing element that triggers delivery of the cryogen and/or the light. Rapid cycling of heating and cooling cycles over a single area before the tissue temperature equilibrates can be implemented to advantageously avoid freezing or burning the tissue.

Other aspects of the invention include methods corresponding to the devices and systems described above, and various applications for this approach.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Figure 1:
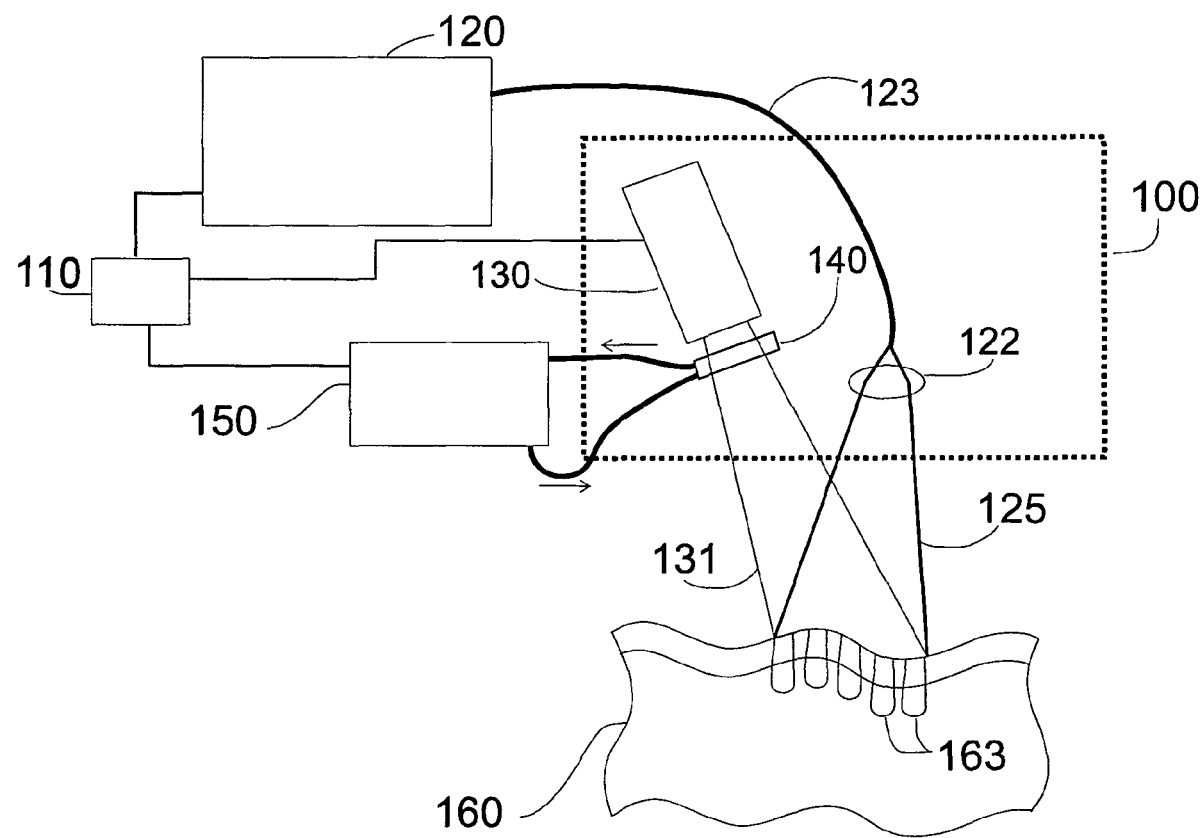
FIG. 1 illustrates an embodiment of the invention for creating fractional treatment zones.

FIG. 1 illustrates an embodiment of the invention. This embodiment includes an optical delivery system and a cryogen delivery system. In the example of FIG. 1, the optical delivery system includes optical source 120. The optical delivery system of FIG. 1 also includes light guide 123 and lens 122. Light guide 123 delivers light 125 from the optical source 120 to the delivery lens 122. The delivery lens 122 delivers light 125 to a target tissue 160.

In the example of FIG. 1, the cryogen delivery system includes a cryogen container 130 and a patterning element. The cryogen delivery system of FIG. 1 includes a mask 140 as the patterning element. The cryogen delivery system of FIG. 1 also includes a temperature control system 150 for heating the mask 140. The cryogen container 130 is controlled by the control unit 110 and sprays a cryogen 131 towards a mask 140 and towards the target tissue 160. The mask 140 patterns the cryogen 131 by allowing part of the cryogen 131 to pass through the mask to reach the target tissue 160. The patterned cryogen 131 creates a patterned cooling profile within the target tissue 160.

The light 125 irradiates a portion of the target tissue 160, including regions cooled by the patterned cryogen 131. Thus, the patterned cryogen 131 and irradiating light 125 together create a pattern of treatment zones 163. The temperature of the mask 140 may be controlled by a temperature control system 150 that may circulate a temperature control fluid to the mask. The cryogen container 130, the temperature control system 150, and the optical source 120 may be coordinated by the control unit 110. A handpiece 100 delivers both the patterned cryogen and irradiating light to the target tissue, and moves over the tissue to treat different locations. The device elements described in FIG. 1 may be located inside or outside the handpiece 100.

In FIG. 1, the cryogen 131 creates a pattern of cooled regions in the target tissue 160. Light 125 heats the target tissue 160 in both cooled regions and uncooled regions. The irradiated cooled regions may thus become heated relative to their temperature prior to treatment, but they are still cooler than the irradiated uncooled regions and may also be cooler than the unirradiated, uncooled regions. Parameters for the system include, for example, pulse duration and wavelength of the light 125, pulse duration of the cryogen 131, pattern of the mask 140, and relative timing of the delivery of the patterned cryogen with respect to the irradiating light. These can be chosen based on the desired treatment pattern within the skin. Examples of such parameters are given in the description for FIG. 4a below.

The control unit 110 can control the parameters of the optical delivery system and/or the cryogen delivery system. In this example, the control unit coordinates the optical source 120, the cryogen container 130, and/or the temperature control system 150. Pulse parameters for the optical source 120 include, for example, pulse intensity, pulse rate, and/or pulse duration. The control unit 110 may also control the timing for triggering the optical source 120 relative to triggering the spraying from the cryogen container 130. In a preferred embodiment, the cryogen 131 is sprayed onto the target tissue 160 prior to the irradiation by the light 125 and/or the cryogen 131 evaporates before the optical light source 120 is pulsed. Spraying the cryogen 131 prior to irradiation and/or allowing the cryogen 131 to evaporate prior to triggering the irradiation reduces the optical scattering of the light 125 that might occur from the cryogen 131 if the cryogen 131 were sprayed at the same time as irradiation by the light 125. It also avoids potential overheating by the light 125 if the heating were done prior to the cooling with the cryogen 131. Other embodiments may apply the irradiation before, during, and/or after the cooling by the cryogen 131 to more efficiently use the thermal energy of the light 125.

The control unit 110 is pictured as a single unit, but the functions of the control unit 110 may be divided into two or more separate components that may or may not communicate. An advantage of having the control unit 110 be a single device or a communicating set of devices is that the timing between the actions of the elements of the apparatus can be implemented. For example, the cryogen container 130 can be triggered to spray cryogen 131 at a particular time relative to the triggering of the optical source 120 to emit light 125. The variation of timing between the cryogen 131 and the emission of light 125 can be used to achieve a desired pattern of tissue treatment within the target tissue 160. The control unit 110 can be a computer that communicates via serial connections (e.g. USB ports) to the optical source 120, cryogen container 130, and temperature control system 150.

Figure 2:
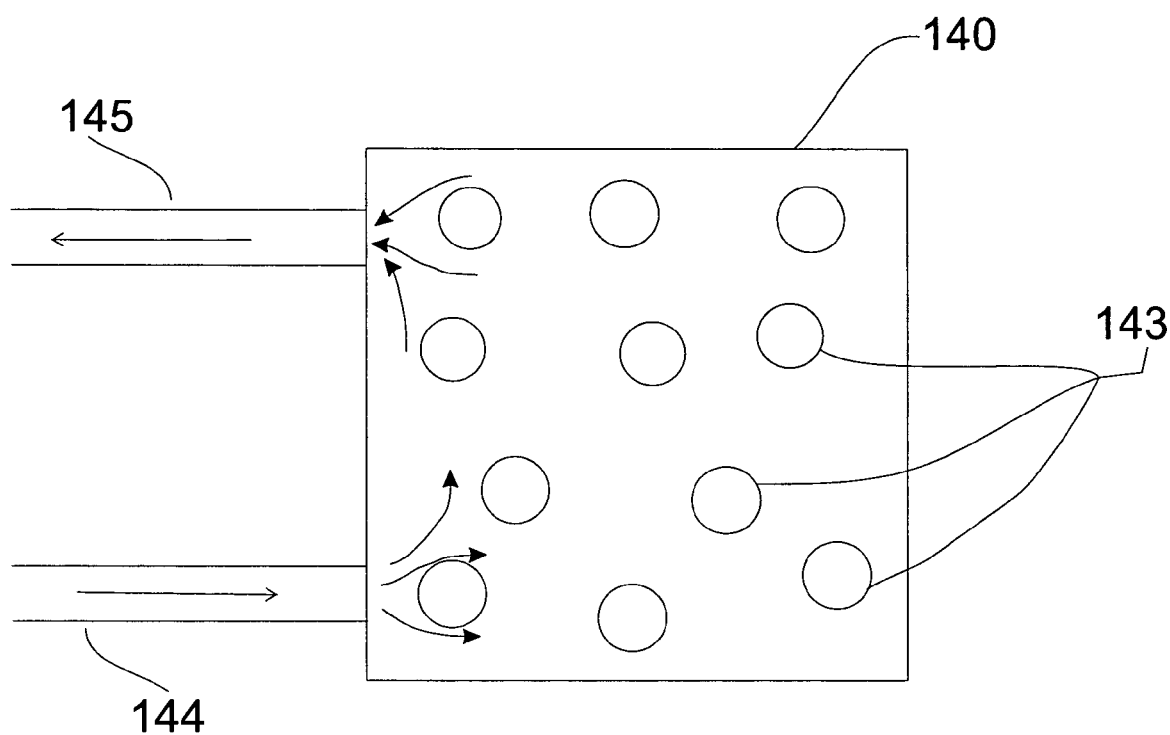
FIG. 2 illustrates an embodiment of the mask of FIG. 1 with ports for heating fluid.

The temperature control system 150 can desirably heat the mask 140 to reduce condensation of water vapor on the mask 140, which can clog the mask and prevent the cryogen 131 from passing through. The temperature control system 150 can be a heater and a pump to circulate a temperature control fluid to the mask 140. The mask 140 can be hollow and allow circulation of the temperature control fluid through the mask 140. As shown in FIG. 2, the mask 140 can include fluid inlet port 144 and a fluid outlet port 145 to allow the circulation of the temperature control fluid within the mask. The mask apertures 143 can be constructed such that each aperture 143 is sealed around its perimeter to prevent leakage of the circulating temperature control fluid out of the mask 140 and open in its center to permit passage of the cryogen 131.

Alternatively, the mask 140 can be made of a solid material with holes drilled to form apertures 143 and the temperature control fluid may flow adjacent to the mask 140 to heat the mask through thermal conduction. The temperature control fluid may be a gas or a liquid and can be, for example, water, nitrogen, or Freon. Choice of fluid can be made based on the thermal characteristics of the fluid and the temperature range over which operation is desired.

The optical source 120 can be, for example, a flashlamp or a laser. The wavelength or wavelength range of the optical source can be chosen based on absorption parameters of the tissue and the particular target. For example, if non-selective heating is desired, then light at a water absorbing wavelength can be used, such as in the range of the water absorption peak around 1.45 μm, particularly wavelengths in the range of 1.4-1.6 μm, which are accessible using InGaAs semiconductor laser diodes, Er:Glass lasers, and/or erbium-doped fiber lasers. This wavelength region is desirable because of the available light sources and the absorption characteristics in water-based tissue, such as human skin. Light at nonselectively absorbed wavelengths, such as for example wavelengths in the range of about 1.2-10.6 μm, can be used to create uniform heating within the tissue and more predictable damage patterns than a selectively absorbed wavelength.

In other configurations, selectively absorbed wavelengths (i.e. wavelengths that are selectively absorbed by particular dermatological features within the tissue) can be used. For example, 570-620 nm dye lasers can be used to treat blood vessels selectively. Thus, spatial patterning of the treatment can be combined with selective photothermolysis. This can be desirable for allowing increased levels of treatment, while avoiding overtreatment and bulk heating of the target tissue 160.

Following a first treatment application, the handpiece 100 can be moved to a second portion of the target tissue to be treated by a second treatment application. The handpiece 100 may also include a velocity- or position-sensing element (not shown) that allows the handpiece 100 to be fired automatically as the handpiece 100 is moved continuously over the surface of the skin. For this purpose, the invention may incorporate a velocity- or position-sensing element such as that described in copending U.S. patent application Ser. No. 11/020,648, entitled "Method and apparatus for monitoring and controlling laser-induced tissue treatment," which is incorporated herein by reference.

The cryogen container 130 is triggered by a signal from the control unit 110 to spray a burst of cryogen 131 towards the mask 140 and the target tissue 160. The cryogen container 130 can be, for example, a vessel for containing compressed cryogen and an electronically controlled valve for releasing the cryogen 131. The cryogen 131 can be, for example, Freon or R134a.

Figure 3:
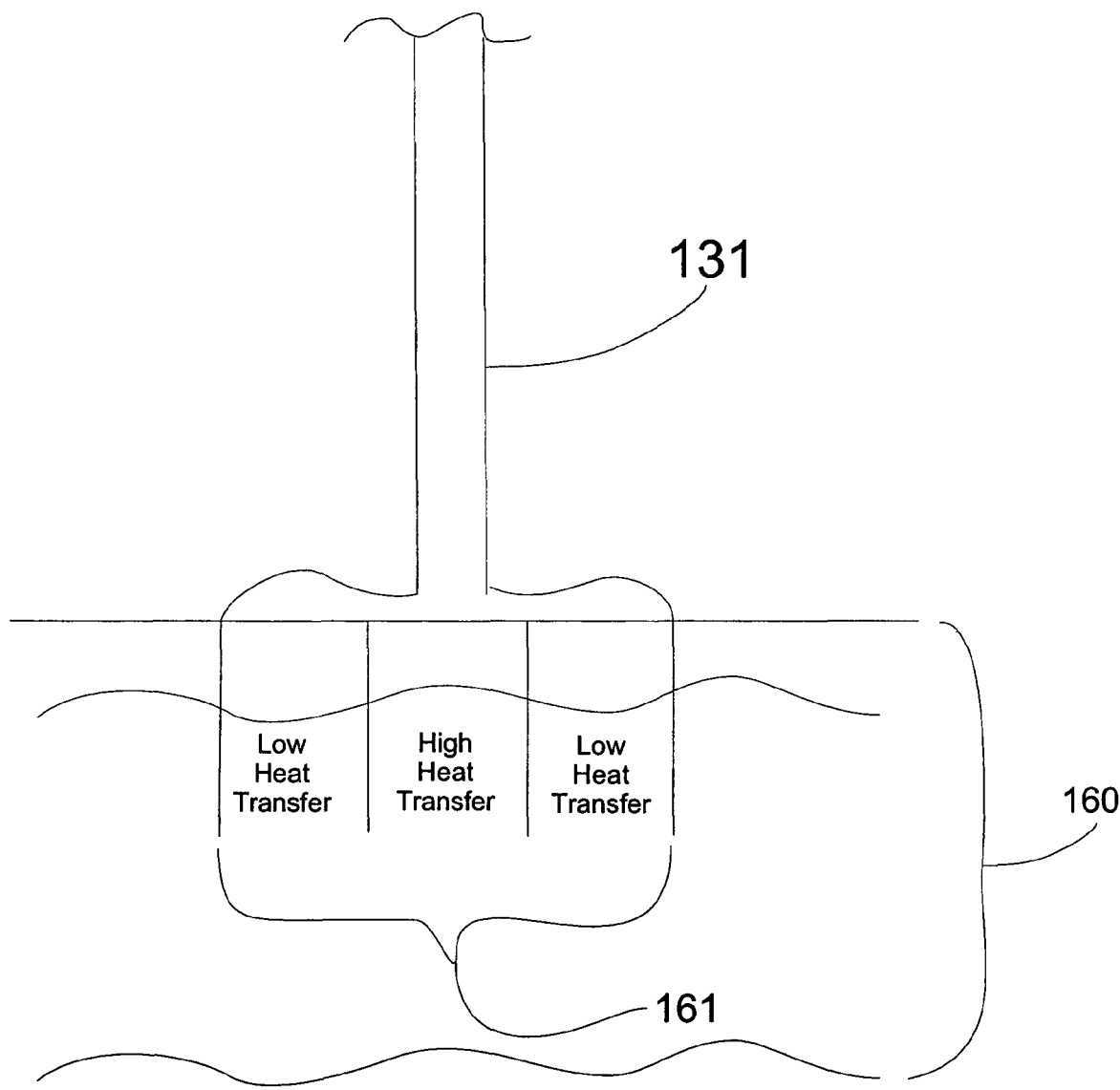
FIG. 3 illustrates heat transfer to the skin from a part of a patterned cryogen.

FIG. 3 illustrates the case where the flow of the cryogen 131 over the surface of the skin is desirably configured such that there are areas of intense cooling (i.e. high heat transfer from the target tissue 160 to the incident cryogen 131) and areas of less intense cooling. Variations in the distribution pattern for the cryogen 131 can be created by controlling the velocity of the cryogen 131 through the adjustment of the pressure of the cryogen 131 in the cryogen container 130. In other configurations, the distribution of cryogen can be uniform across each part of the pattern of cryogen 131. The ability to control the distribution of cryogen allows for variations in treatment response of the target tissue 160 by varying the pattern, size, and/or shape of the resulting treatment zones 163.

Figure 4A:
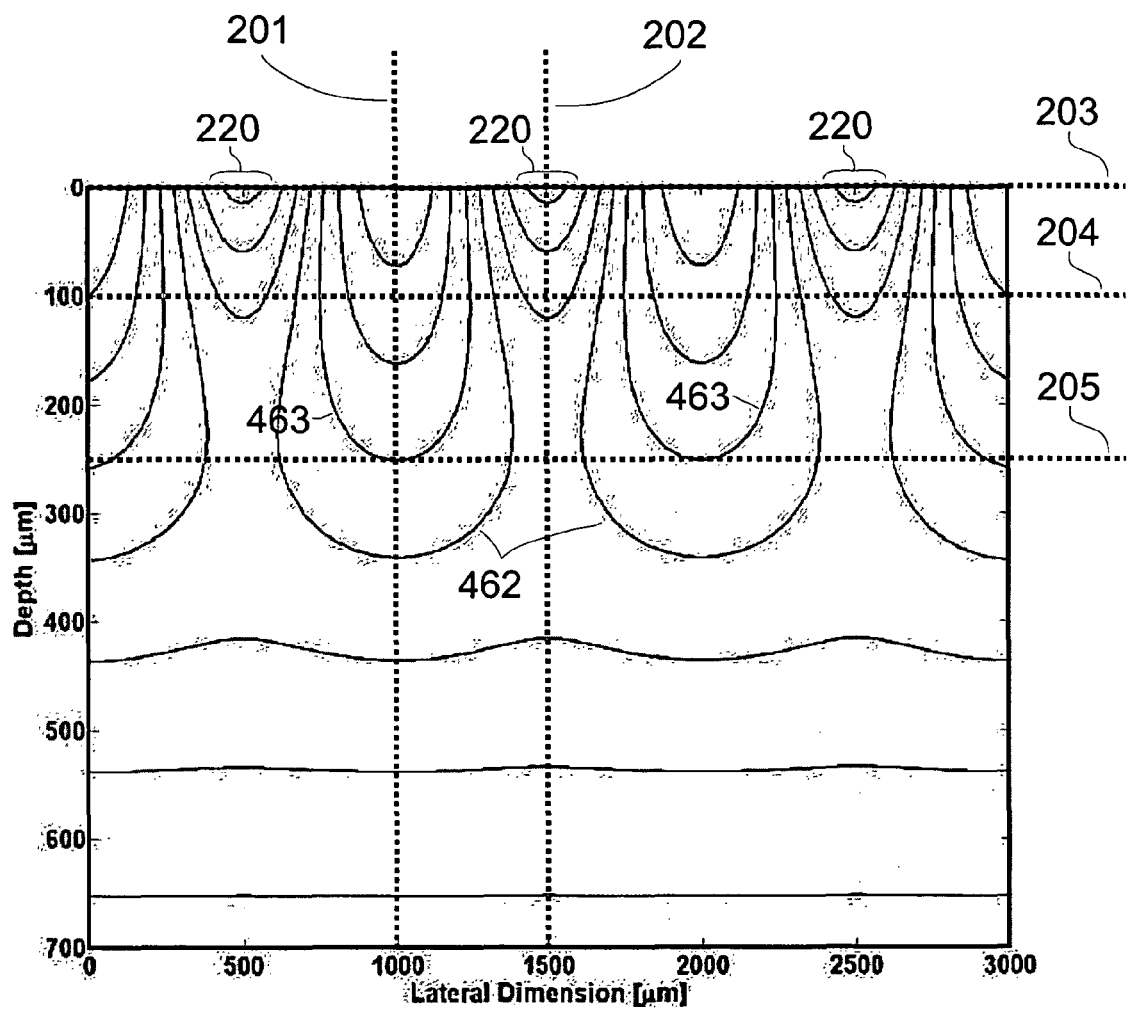
FIGS. 4a, 4b, and 4c show computer-modelled temperature distributions in target tissue.
Figure 4B:
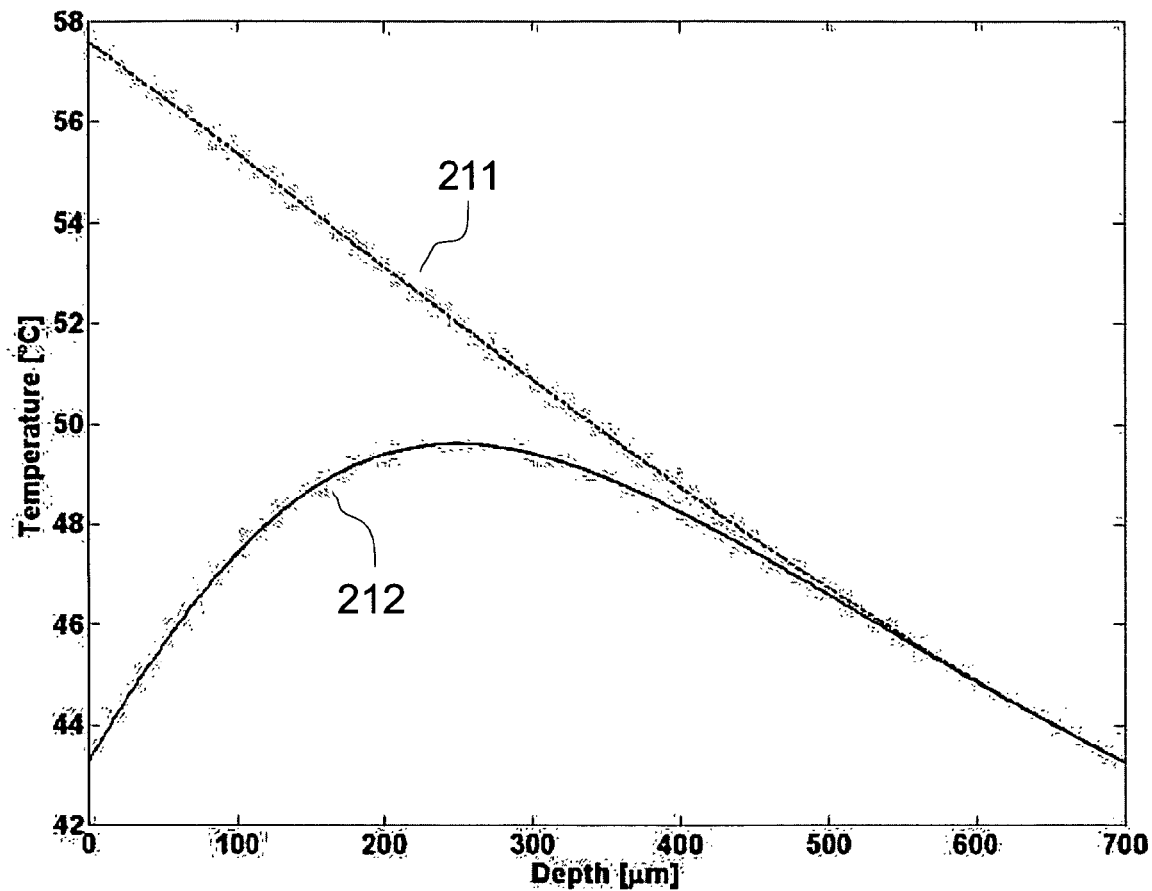
Figure 4C:
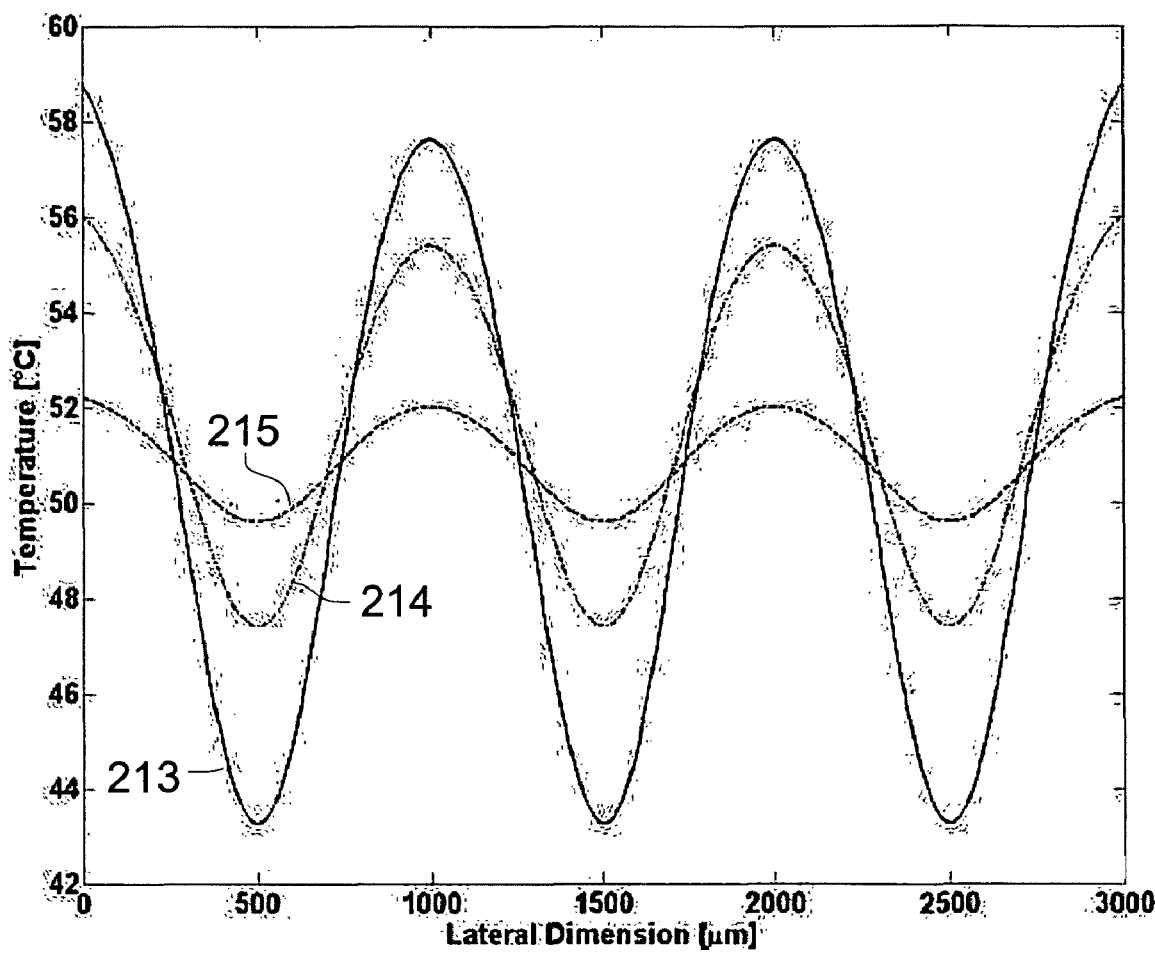

FIGS. 4a, 4b, and 4c describe the results of a computer simulation of an embodiment of the invention in which the cryogen 131 is deposited in a striped pattern with the direction of the stripes pointed in the direction perpendicular to the plane of the paper. FIG. 4a shows the thermal contours in a cross-section of the target tissue 160 at a time immediately after treatment with the cryogen 131 and the light 125. The temperature contours are drawn every 2° C. in the range of 44 to 56° C. The locations of applied cooling 220 are illustrated in the diagram. The regions just below the locations of applied cooling 220 are the lowest temperature regions in the cross section of the target tissue 160 for the conditions modeled in FIG. 4a.

In FIG. 4a, cut lines are drawn in both the vertical and horizontal directions to describe the locations for the thermal profiles of FIGS. 4b and 4c. FIG. 4b plots the thermal profile as a function of depth into the target tissue of FIG. 4a at the center of a cooled region (along cut line 202) and at the midpoint between adjacent cooled regions (along cut line 201). The cooled cut line 202 penetrates the target tissue 160 vertically through the center of a location of applied cooling 220. The heated cut line 201 penetrates the target tissue 160 vertically from a location halfway between centers of adjacent locations of applied cooling 220. The temperature profiles along heated cut line 201 and cooled cut line 202 are plotted in FIG. 4b as temperature profiles 211 and 212, respectively.

FIG. 4c plots the thermal profile in the target tissue of FIG. 4a at three depths in the target tissue. Horizontal cut lines 203, 204, and 205 correspond to the temperature profiles 213, 214, and 215, respectively, that are plotted in FIG. 4c. Horizontal cut line 203 is just below the surface of the target tissue (i.e. at approximately 0 μm depth). Horizontal cut line 204 is at approximately 100 μm depth. Horizontal cut line 205 is at approximately 250 μm depth, which corresponds to the approximate peak of the cooled temperature profile 212 shown in FIG. 4b.

The computer simulation used analytical solutions to Green's functions to model thermal dissipation into and within the tissue. More detailed information regarding the model used in this calculation can be found in *Optical Thermal Response of Laser—Irradiated Tissue* (Ashley J. Welch and Martin J. C. Van Gemert, Editors, Plenum Press, NY, 1995), which is incorporated herein by reference. In this example, the pattern of the cryogen 131 is a stripe pattern that is deposited with the direction of the lines pointed in the direction perpendicular to the plane of the paper. The width of each of the stripes of the pattern is 200 μm and the cryogen 131 is assumed to have a uniform distribution across each of the 200 μm stripes. The cryogen 131 is R134a with a temperature of −15° C. and in contact with the skin for 200 ms just prior to the application of the beam of light 125. The optical source 120 is an erbium-doped fiber laser operating at a wavelength of 1.552 μm.

The beam of light 125 that is heating the tissue has a uniform intensity distribution across its entire width of 3.35 mm and is centered at 1500 μm in FIG. 4a. The beam width was chosen to create contours at the outside of FIG. 4a that were similar in depth to the contours between the locations of applied cooling 220. The heating with the light was assumed to follow an exponential absorption decay with depth into the skin based on the absorption at the chosen wavelength. The absorption parameter was 11.6595 cm$^{-1}$, which approximately corresponds to the absorption of 1.552 μm light in human skin. The thermal diffusivity of the target tissue 160 was $1.1*10^5$ μm²/s, which corresponds to the thermal diffusivity of human skin.

As shown in FIG. 4a, various treatment zones can be created. For example, if a desired treatment result only occurs for temperatures above 52° C., then separated treatment zones, as defined by the 52° C. contours 463, of approximately 250 μm depth and 500 μm width would be created using the parameters above.

In this application, the term "treatment zone" is intended to describe a region of target tissue within which a desired treatment effect takes place and just outside of which, the desired treatment effect does not take place. For example, the desired treatment effect could be collagen denaturation, tissue necrosis, stimulation of the release of a particular cytokine or growth factor, or stimulation of heat shock proteins. These treatment effects each have a temperature at which the event occurs for the time frame of a particular lesion. Larger lesions will have longer time constants, which will allow the thermal effects longer time to interact with the target tissue 160 and will likely create larger treatment zones 163. Different types of treatment will require different temperatures to be achieved to create treatment zones 163. Due to differences in temperature time relationships for different types of treatment effects and different patterns, different treatment parameters than the ones presented here will be used to achieve a particular treatment result. In addition, there are variations from patient to patient and even within a particular patient. So it is desirable to create a flexible implementation that allows control over the parameters described above, particularly laser pulse duration, cryogen spray duration, and timing between the triggering of the laser pulse and the cryogen spray.

Figure 5:
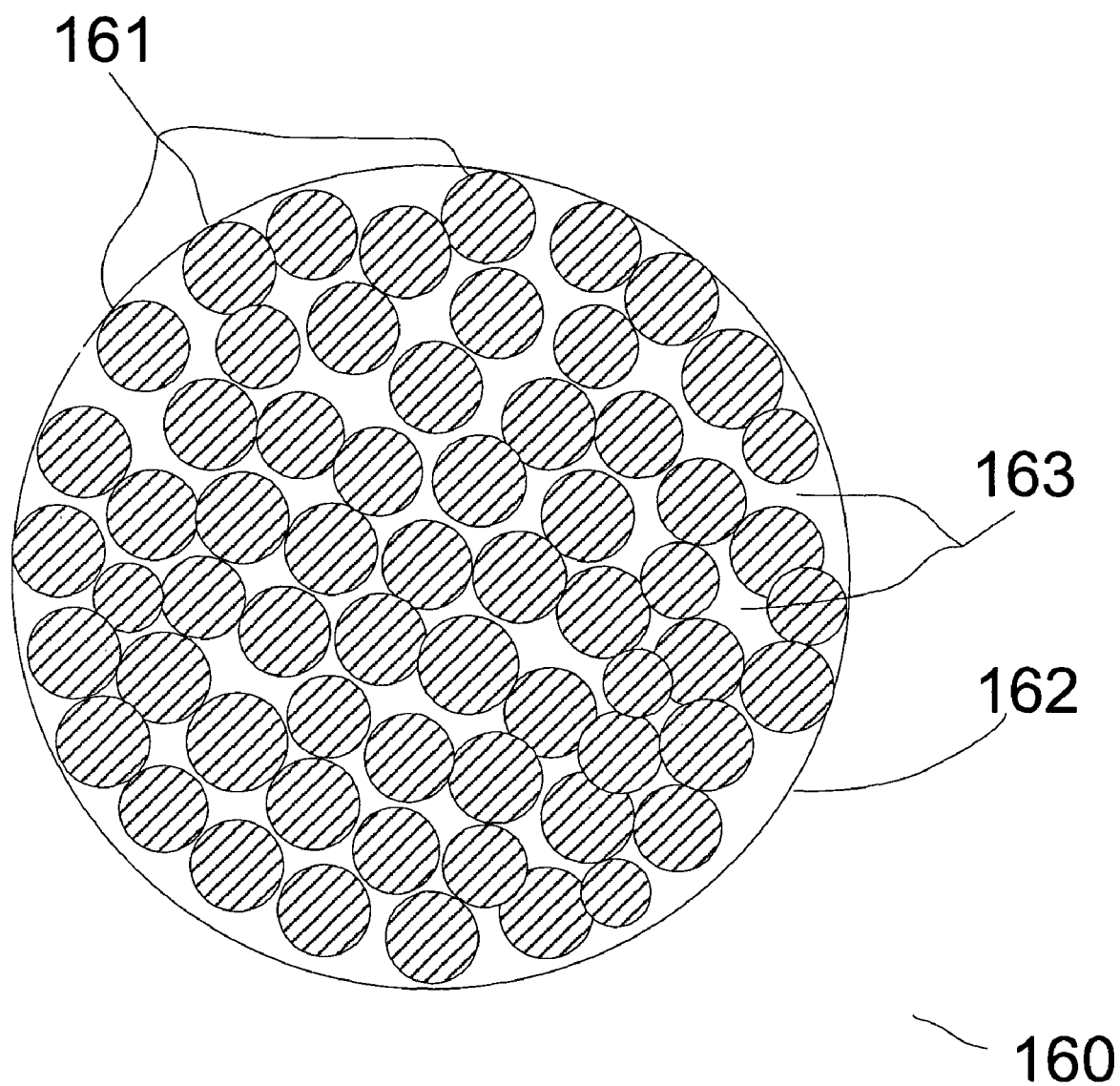
FIG. 5 is a top view of a pattern of fractional treatment according to the invention.

FIG. 5 shows a top view of a treatment on target tissue 160 according to an embodiment of the invention. A pattern of cryogen 131 is incident on the target tissue 160 to create cooled regions 161. Light 125 is incident on the target tissue 160 to create a heated region 162 and treatment regions 163.

The cooled regions 161 are where cryogen 131 is incident on the skin. Note that the cooled regions 161 may be heated relative to body temperature due to the effects of the irradiating light 125. The treatment zones 163 typically occur between and around the cooled regions 161. In some configurations, however, the treatment zones 163 may overlap the cooled regions 161 because the zones of cooling are based on where the cryogen 131 is incident on the surface of the skin, which may not correspond with the treatment regions 163 if, for example, the thermal effects of the cryogen 131 are not uniform over each cooled zone 161.

The fill factor is the area of coverage of treatment zones 163 as a percentage of the heated area 162 at a desired depth. Both the fill factor and the shape (not shown in FIG. 5) of the treatment zones 163 within the tissue can be chosen based on the condition being treated and the tolerance of the selected target tissue 160. For example, if the target tissue 160 is a human forearm and the treatment is a cosmetic treatment of pigmented lesions, then a relatively low fill factor and a relatively shallow treatment zone 163 of 100 μm depth would be appropriate to lessen the risk of scarring in this sensitive area. If the target tissue 160 is human facial skin and the treatment is a cosmetic treatment of wrinkles, then a larger fill factor and a deeper treatment zone 163 would be appropriate because the treatment will be more effective if it addresses deeper into the dermis and covers a larger percentage of the target tissue 160.

Other fractional resurfacing systems are limited to lower fill factors because the treatment zones 163 produced by those systems are wider at the DE junction than within the dermis. As shown in FIG. 4a for the 50° C. contours 462, the treatment zones 163 created by this approach can be smaller at the DE junction, which is typically located 50-100 μm below the skin surface for human facial skin, than within the dermis. This can desirably allow a larger fill factor to be used than is used in other fractional resurfacing systems without resorting to inconvenient optics with high numerical apertures. Treatment densities of 50-80% can be used in aggressive treatments. In these cases, care should be taken to reduce the risk of scarring by proper post-treatment care and infection prevention. Typical treatments will have fill factors in the range of 5-30%.

In FIG. 5 discrete treatment zones 163 are separated from one another by cooled regions 161. In some treatments, it is desirable to create a high density of discrete treatment regions 163 that are relatively small. In a preferred embodiment, the density of discrete treatment regions is 100-4000 per cm² and more preferably in the range of 300-1000 per cm². For high fill factors, the treatment zones may not be discrete, but may be continuous and within the heated region 162. Fractional treatment is still accomplished by sparing tissue within the heated region 162 between the portions of the treatment zone 163.

Rapid cycling of heating and cooling cycles over a single area before the tissue temperature equilibrates may be implemented to advantageously avoid freezing or burning the tissue undesirably.

Figure 6:
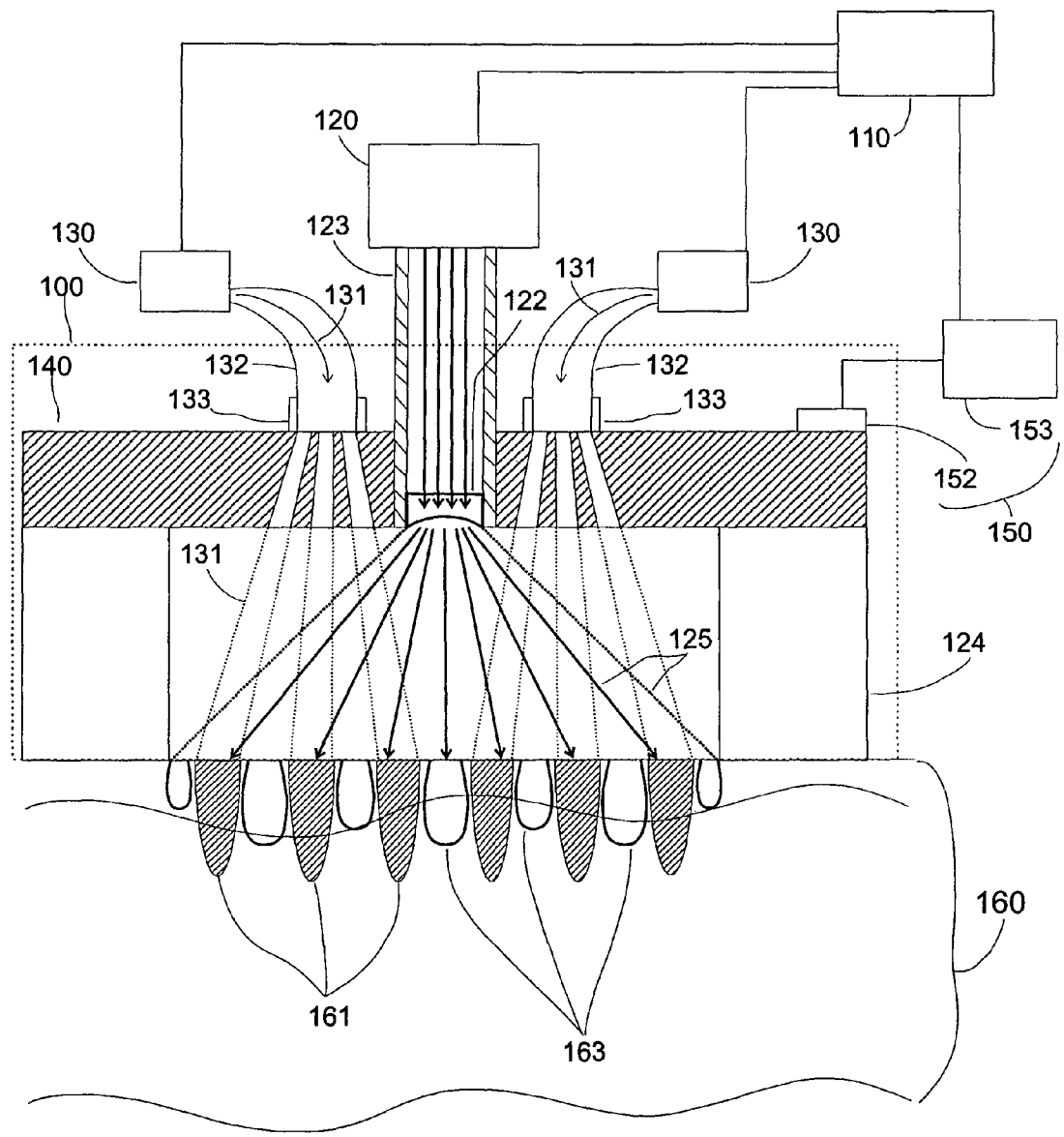
FIG. 6 is an illustration of another embodiment of the invention for creating fractional treatment zones.

FIG. 6 illustrates another embodiment of the invention. In this embodiment, the temperature control system 150 is an electrical source 153 and a resistive heater 152. The resistive heater 152 is powered by the electrical source 153 and is in thermal contact with the mask 140. In this embodiment, a control unit 110 triggers one or more cryogen containers 130 to spray cryogen 131 into cryogen delivery tubes 132. The cryogen delivery tubes 132 can be configured to connect to the mask 140 using cryogen ports 133 and are configured to deliver cryogen 131 to the mask 140 and the target tissue 160. The cryogen 131 is patterned by the mask 140 such that the cryogen forms a pattern of cooled regions 161 on the target tissue 160. As described for FIG. 1, the control unit 110 can set parameters of the optical source 120 and can trigger the optical source to emit light 125. The light 125 is guided to the delivery lens 122 using an optional light guide 123 or can be delivered through free space. The delivery lens 122 directs the light 125 to the target tissue 160 to form treatment zones 163. The spacer 124 creates a predetermined separation between the mask 140 and the target tissue 160 and/or between the light delivery lens 122 and the target tissue 160 to allow the creation of a predetermined pattern of cooled regions 161 and/or treatment zones 163. One or more of the elements described in this paragraph can be part of the handpiece 100.

The delivery lens 122 shown in FIG. 1 is a refractive positive lens. The delivery lens 122 shown in FIG. 6 is a refractive negative lens. The type of delivery lens 122 can be chosen based on the desired thermal profile for the treatment and the spatial constraints of the handpiece 100. Mirror based or diffractive lenses could equivalently be used for the delivery lens 122.

Depending on the regularity of the spacing of the cryogen pattern and the chosen treatment parameters, the shape and/or depth of the treatment zones 163 can be designed to be substantially uniform across the heated region 162. For example, if the regular pattern of FIG. 4a were extended for more than three locations of applied cooling 220 and the heated region 162 were enlarged accordingly, the treatment zones described by the 52° C. equithermal contours of the model would be substantially uniform. The shapes and/or depths of the treatment zones 163 can be alternatively designed to be substantially nonuniform across the heated region 162 as shown in FIG. 6. This type of pattern could be created, for example, using the cryogen spray pattern of FIG. 5, wherein the size of each cooled region 161 and the spacing between adjacent cooled regions 161 is nonuniform.

In alternate embodiment (not shown), the mask 140 can be heated using a portion of the light 125. In comparison to the fluid circulating type of temperature control system 150 of FIG. 1, an advantage of using the resistive heater 152 or the light 125 to heat the mask 140 is that the hardware is less complicated and not subject to leaking. An advantage of the fluid circulating type of system is that fluid will quickly heat the mask 140, particularly in the areas around each aperture 143.

The temperature control system 150 of FIGS. 1 and 6 is optional. In other embodiments (not shown), the temperature of the mask 140 is not controlled. The mask 140 can be allowed to equilibrate to a desired temperature between firings of the cryogen container 130, for example to prevent clogging of the mask.

A circular nozzle with a single circular hole that is used to deliver a cryogen 131 is not considered to be within the definition of a mask 140. A more intricate pattern is required. Similarly, the application of cryogen to cover a single circular or rectangular region or other similar shapes is not considered to be within the definition of a patterned cryogen.

In yet another configuration (not pictured), a vacuum chamber may form a seal between the handpiece 100 and the target tissue 160. The seal could also include the contents of the cryogen delivery tubes 132. A vacuum (not pictured) can be connected to the vacuum chamber to remove water vapor from the air surrounding the portions of the mask 140 that allow the cryogen 131 to pass through so that water vapor does not condense on the mask 140.

Figure 7A:
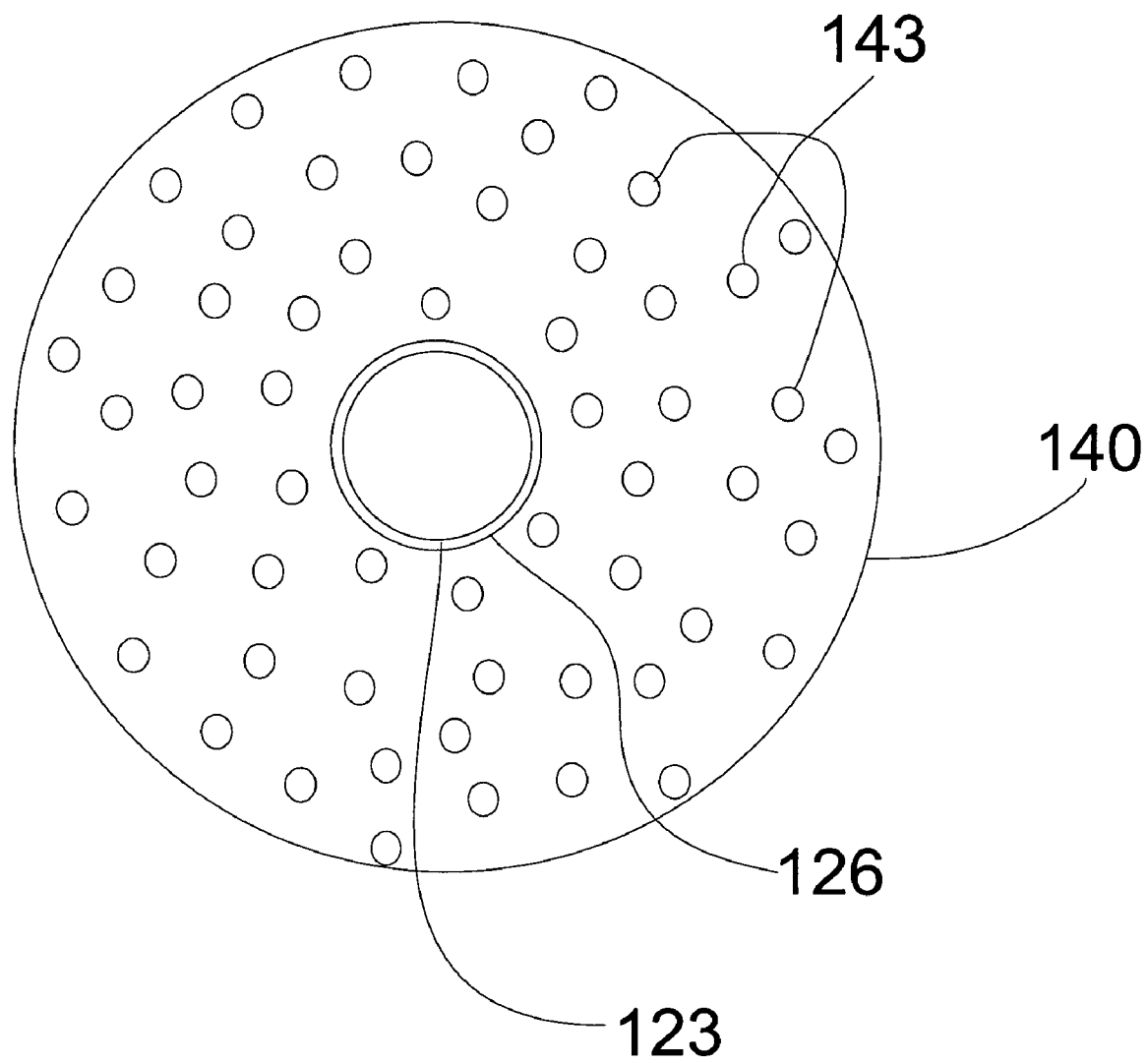
FIG. 7a is an illustration of a mask that can be used in the system of FIG. 6.
Figure 7B:
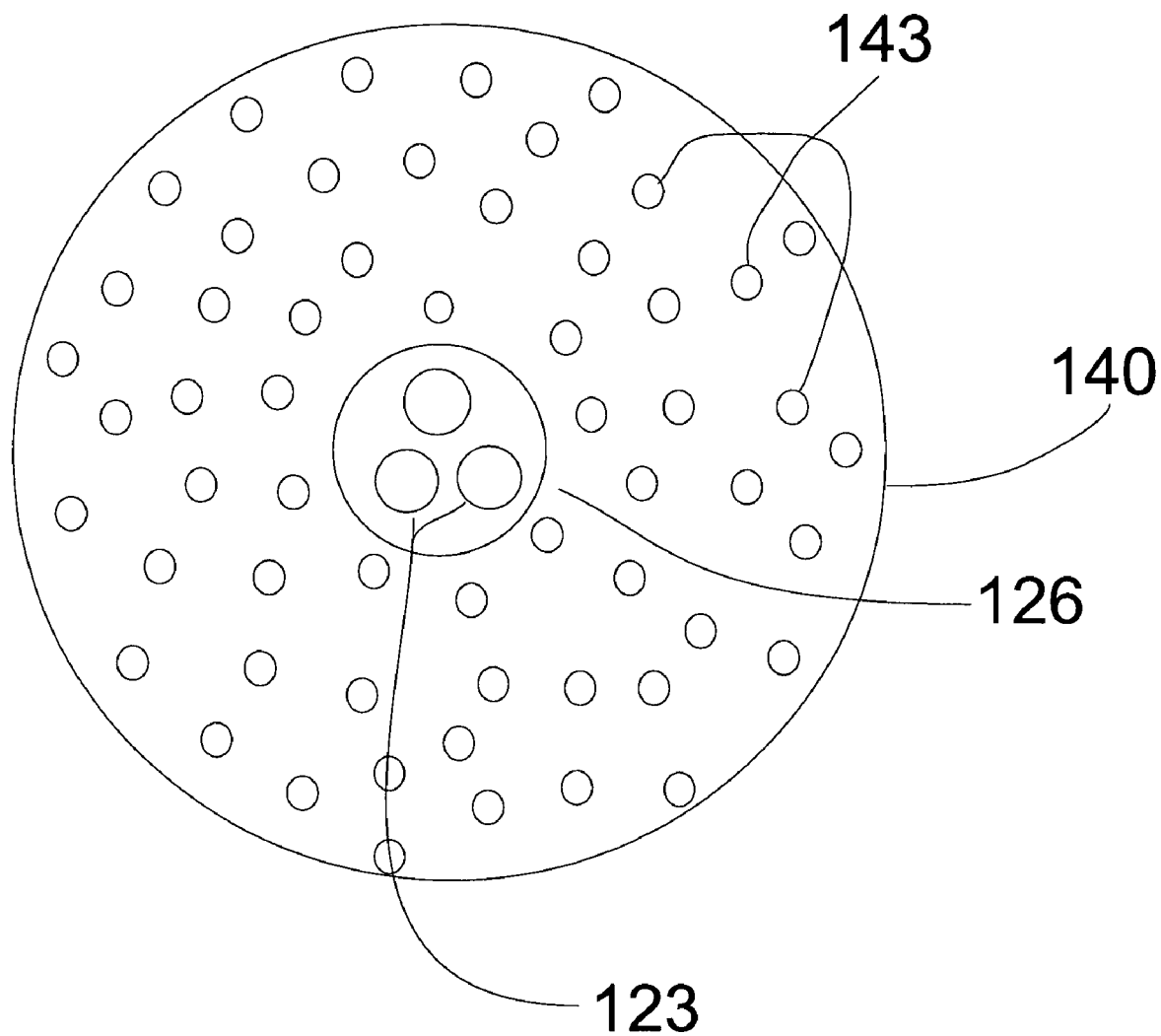
FIG. 7b is an illustration of a mask that could be used in an embodiment with multiple light guides.

FIGS. 7a and 7b illustrate embodiments of the mask 140. The mask 140 can be made of metal or plastic with apertures 143 that are machined through the mask 140 to distribute the cryogen 131 in the desired pattern on the target tissue 160. A guide tube 126 can be machined through the mask 140 to hold one or more light guides 123. Multiple light guides 123 (as illustrated in FIG. 7b) may be desired to create a more uniform optical distribution across the tissue in contrast to a sharply peaked distribution that could be obtained if, for example, only one single mode fiber were used (as illustrated in FIG. 7a). The mask 140 can contain one or more light guides 123 and one or more delivery lenses 122 (not illustrated in FIGS. 7a and 7b). Multiple light guides 123 could be, for example, multiple optical fibers that are used for delivery from two or more optical sources 120 each emitting a different wavelength of light 125. The multiple wavelengths of light 125 would have different optical penetration depths and/or be absorbed in different chromophores within the target tissue 160. Thus, multiple wavelengths could be used, for example, to address one or more chromophores within the tissue or be used to achieve non-selective treatment in combination with enhanced treatment of a particular chromophore. A second non-overlapping wavelength range is a wavelength range that does not overlap with the first wavelength range and which has a substantial difference in absorption for water or for a targeted chromophore (e.g., blood or melanin) within the target tissue 160 than the first wavelength range.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

The terms "cryogen" and "cryogen spray" are used interchangeably within this application. In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A method of cosmetic dermatological treatment of a target tissue, comprising:
   spraying a cryogen toward a mask having a plurality of apertures;
   selectively blocking a first portion of the cryogen spray with the mask;
   passing a second portion of the cryogen spray through the plurality of apertures in the mask to define a patterned cryogen that reaches the target tissue and that matches a pattern of the plurality of apertures in the mask at the target tissue, the patterned cryogen that passes through the plurality of apertures creating a pattern of cooled regions with adjacent uncooled regions on the target tissue; and
   irradiating the cooled regions and the adjacent uncooled regions of the target tissue with light, the patterned cryogen and the light cooperating to create a pattern of treatment zones within the target tissue.

2. The method of claim 1 further comprising:
   controlling a timing of the delivery of the patterned cryogen to the target tissue relative to the irradiation of the target tissue with the light.

3. The method of claim 2 wherein the patterned cryogen is delivered to the target tissue before the target tissue is irradiated with the light.

4. The method of claim 2 wherein the patterned cryogen is delivered to the target tissue and evaporates from the target tissue before the target tissue is irradiated with the light.

5. The method of claim 2 wherein the patterned cryogen is delivered to the target tissue at a same time as the target tissue is irradiated with the light.

6. The method of claim 1 wherein the pattern of treatment zones comprises a plurality of discrete treatment zones with a density of between 100-4000 treatment zones per $cm^2$.

7. The method of claim 1 wherein the treatment zones form a continuous pattern.

8. The method of claim 1 wherein spraying the cryogen onto and through the plurality of apertures in the mask further comprises:
   heating the mask.

9. The method of claim 1 wherein treatment zones comprise coagulated tissue within the dermis.

10. The method of claim 1 wherein treatment zones are wider within the dermis than at the DE junction.

11. The method of claim 1 wherein the target tissue is human facial skin.

12. The method of claim 1 wherein irradiating the target tissue with the light comprises:
   irradiating the target tissue with light within a first wavelength range; and irradiating the target tissue with light within a second wavelength range that is non-overlapping with the first wavelength range.

13. The method of claim 8 wherein heating the mask further comprises:
circulating a temperature control fluid to the mask to heat the mask by thermal conduction for delivery of the cryogen through the mask without clogging the mask.

14. The method of claim 8 wherein the mask comprises a hollow structure, and heating the mask further comprises:
circulating temperature control fluid inside the hollow structure for delivery of the cryogen through the mask without clogging the mask.

15. The method of claim 1 wherein the mask is a heated mask, and spraying the cryogen further comprises:
spraying the cryogen onto the heated mask positioned between the spray of cryogen and the target tissue, but without being in contact with the target tissue.

16. The method of claim 1 wherein spraying the cryogen further comprises:
automatically spraying the cryogen at intervals timed relative to the triggering of the irradiation of the target tissue with the light.

17. The method of claim 1 wherein spraying the cryogen further comprises:
spraying the cryogen onto the mask that is a predetermined distance from the target tissue, thereby creating a predetermined pattern of cooled and uncooled regions on the target tissue.

18. The method of claim 1 further comprising:
controlling the velocity of the cryogen spray delivered to create areas of the target tissue that are more intensely cooled relative to adjacent areas of the target tissue that are less intensely cooled.

19. The method of claim 1 wherein irradiating the cooled regions and adjacent uncooled regions of the target tissue further comprises:
applying the light that heats both the cooled regions and the uncooled regions, the uncooled regions being treatment zones that are adjacent to and interspersed with the cooled regions to avoid overheating.

\* \* \* \* \*